United States Patent [19]

Ammann et al.

[11] 4,340,097
[45] Jul. 20, 1982

[54] CONNECTOR MEMBER FOR SEALED CONDUITS

[75] Inventors: David W. Ammann, Boulder, Colo.; Daniel B. Granzow, Ingleside, Ill.

[73] Assignee: Baxter Travenol Laboratories, Inc., Deerfield, Ill.

[21] Appl. No.: 222,395

[22] Filed: Jan. 5, 1981

Related U.S. Application Data

[63] Continuation of Ser. No. 5,749, Jan. 23, 1979, Pat. No. 4,265,280.

[51] Int. Cl.³ ............................................. B65B 3/04
[52] U.S. Cl. .................................... 141/98; 141/382; 156/272.2; 285/3; 285/67
[58] Field of Search ............. 141/1, 98, 114, 311 R, 141/392, 382–388; 222/541; 250/338; 285/3, 4, 67, 325; 156/250, 251, 252, 253, 261, 272, 289, 306; 219/221 LK; 221 LL

[56] References Cited

U.S. PATENT DOCUMENTS

| | | | |
|---|---|---|---|
| 79,343 | 6/1868 | Hamilton | 285/67 |
| 331,998 | 12/1885 | Parsels | 285/67 |
| 3,083,916 | 4/1963 | Neel | 222/541 |
| 3,169,562 | 2/1965 | Gogel | 222/541 |
| 3,364,930 | 1/1968 | Ryan | 222/541 |
| 3,491,752 | 1/1970 | Cowley | 222/541 |
| 3,764,796 | 10/1973 | Gilliam et al. | 222/541 |
| 3,964,643 | 6/1976 | Morane et al. | 222/541 |
| 4,122,980 | 10/1978 | Laverty | 222/541 |
| 4,157,723 | 6/1979 | Granzow | 141/1 |

*Primary Examiner*—Houston S. Bell, Jr.
*Attorney, Agent, or Firm*—Paul C. Flattery; Daniel D. Ryan; Garrettson Ellis

[57] ABSTRACT

An improved connector member is provided for providing sealed and preferably sterile connection between a pair of conduits which each terminate in a hollow, transparent housing where some of the wall portion of each housing comprises an opaque wall portion sealed to the remainder of the housing. The opaque wall portions of each housing are positioned in facing contact with each other and are held in sealed, retentive relationship so that exposure to radiant energy causes them to fuse and open an aperture therethrough. In accordance with this invention, improved retention means are provided to permit the respective housings to be moved together in a path which is generally parallel to the opaque walls into sliding retaining relation. Also, the conduit communicating with the housings may be internally sealed, being openable from the exterior.

18 Claims, 13 Drawing Figures

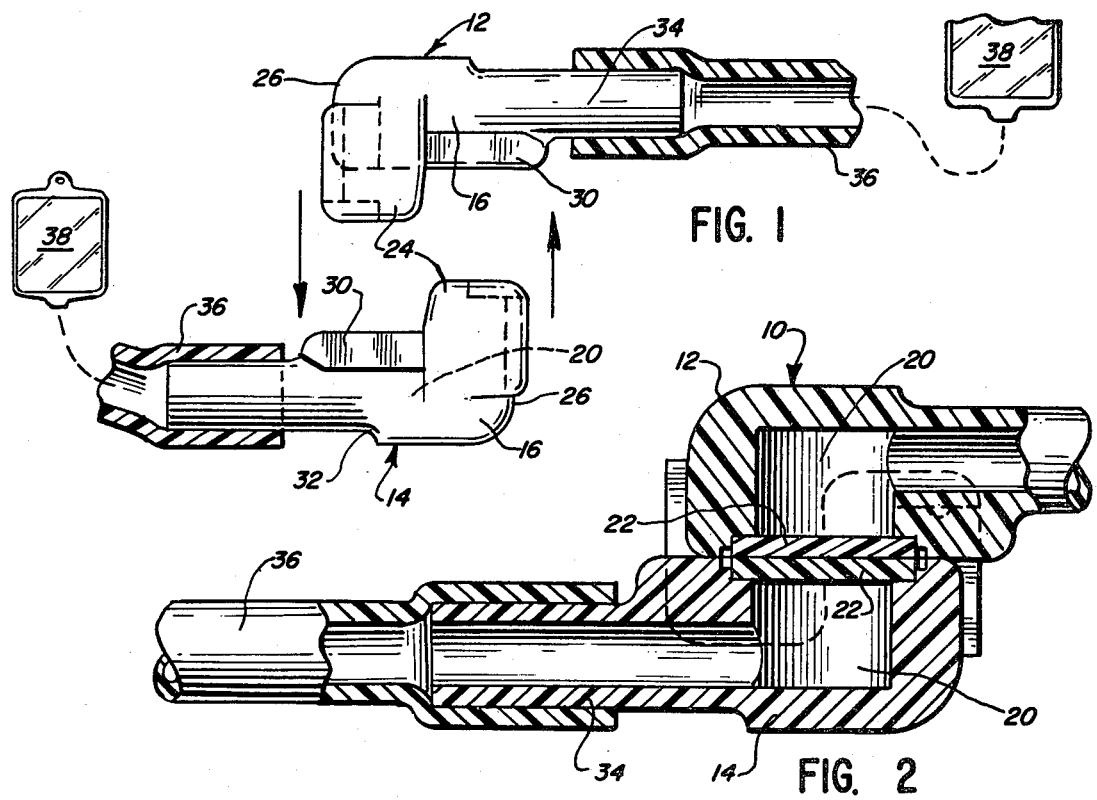
FIG. 1
FIG. 2
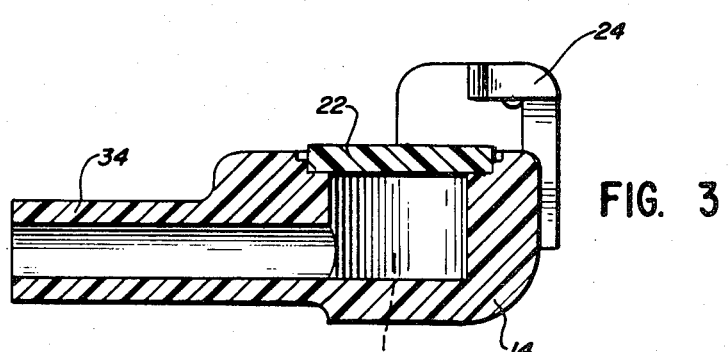
FIG. 3
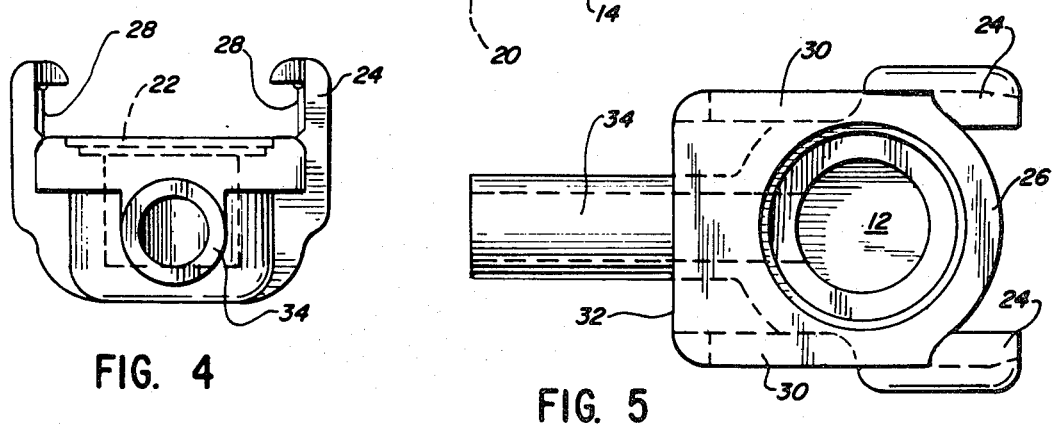
FIG. 4
FIG. 5

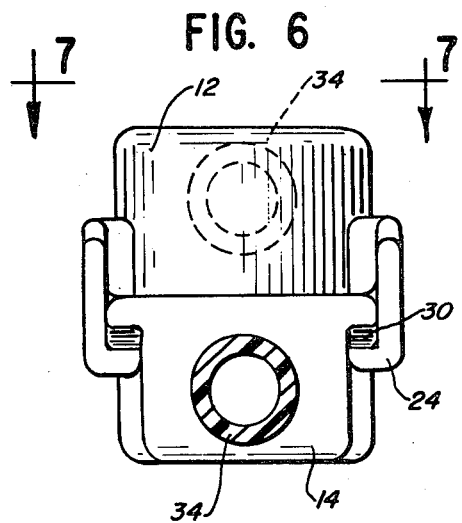
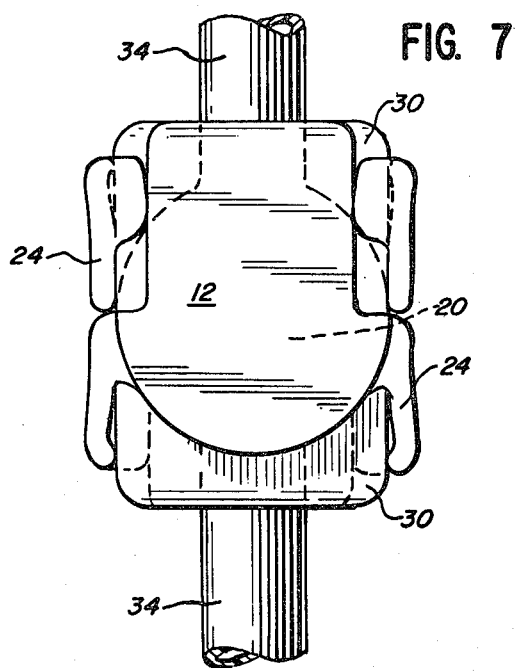
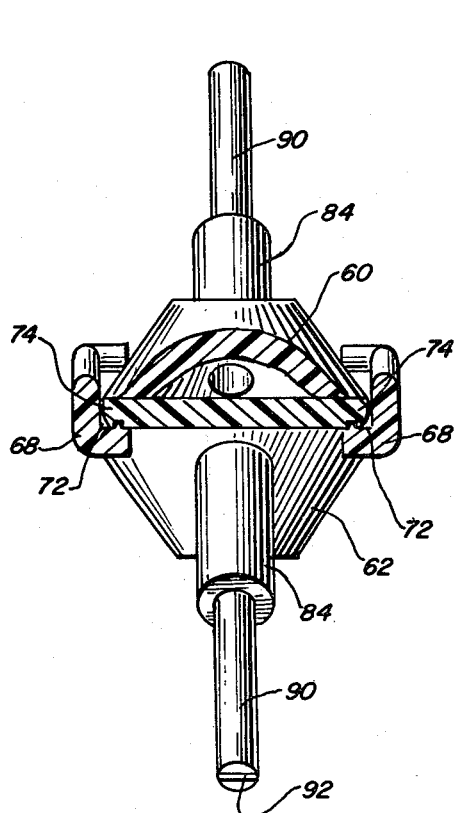
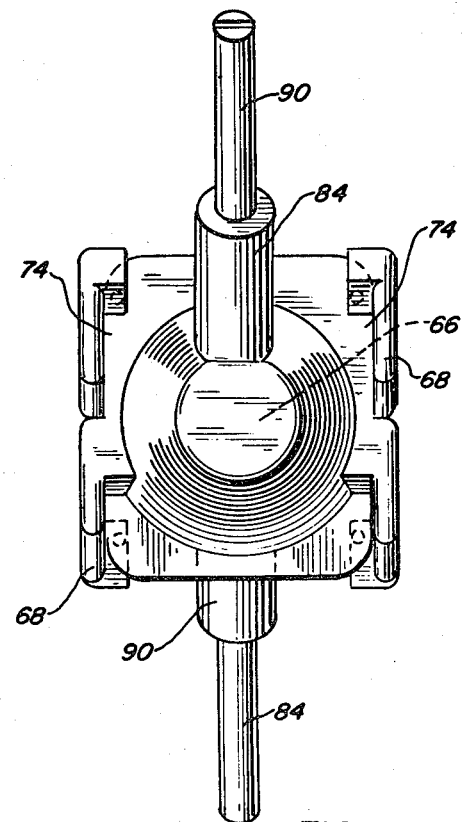

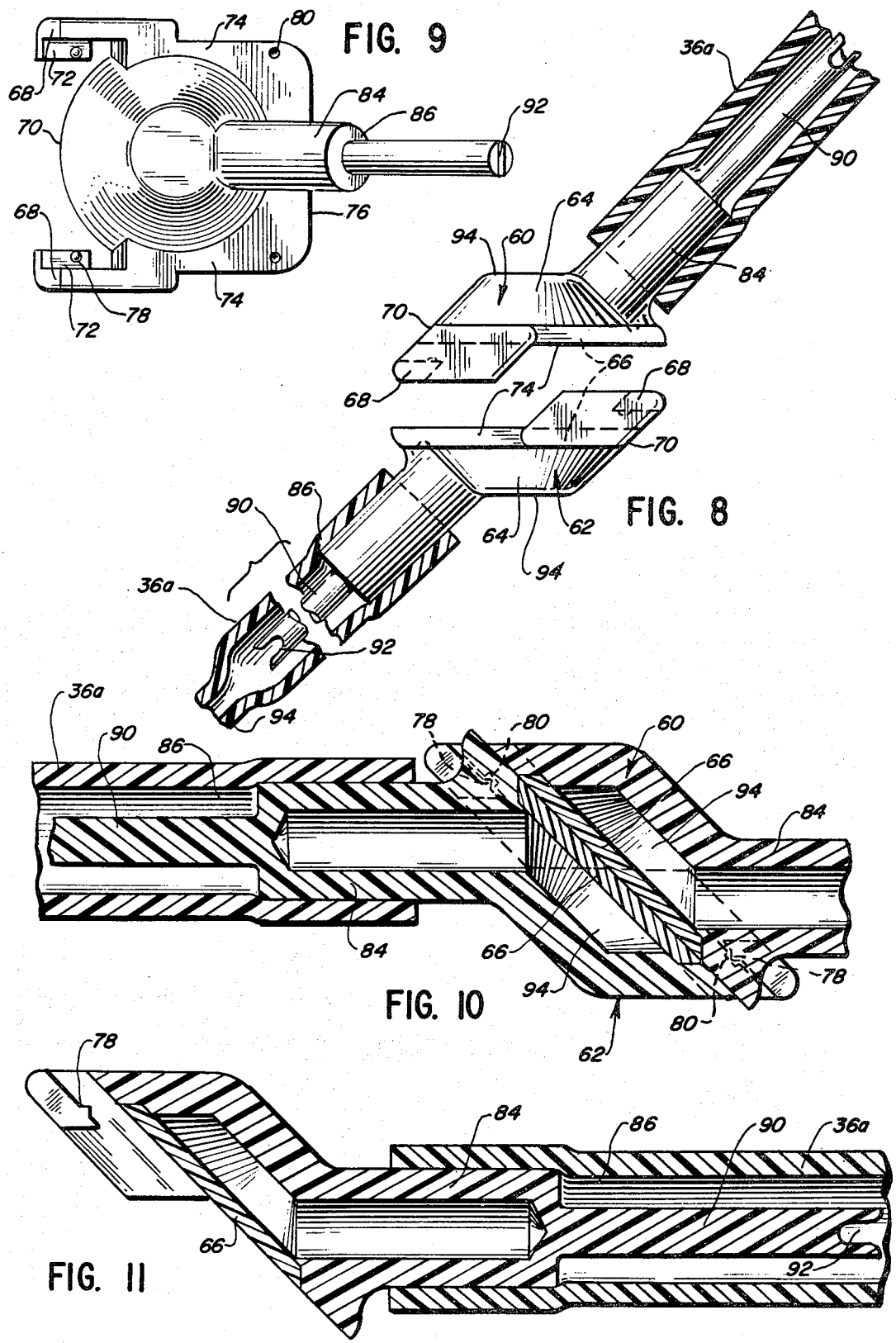

CONNECTOR MEMBER FOR SEALED CONDUITS

This is a continuation of application Ser. No. 055,749, filed Jan. 23, 1979, now U.S. Pat. No. 4,265,280.

BACKGROUND OF THE INVENTION

In U.S. patent application Ser. No. 843,603, filed Oct. 19, 1977 by Daniel B. Granzow, et al., a connector member is shown for providing preferably sterile connection between the ends of conduits, for example, conduits which communicate with blood bags. Accordingly, when sealed, sterile connection is guaranteed, portions of blood, blood components, or other medical materials, for example, can be removed from one container and placed in another in sterile manner, after the connection has been made and a sealed connection provided by exposure to radiant energy as described in the previously cited application.

This present application relates to improvements in the design of the connector member for added convenience and reliability of manufacture and use.

DESCRIPTION OF THE INVENTION

In accordance with this invention, a connector member providing sealed connection comprises a pair of connector elements which, in turn, each include a pair of hollow, transparent housings. The hollow interiors of each of the housings are sealable from the exterior, with some of the wall of each housing comprising an opaque wall portion separating the hollow housing interior from the exterior. Each opaque wall portion is sealed to the remainder of the transparent housing, said housings being positioned together with the opaque wall portions in facing contact with each other and held in sealed, retentive relationship. Accordingly, upon exposure of the connected housings to radiant energy, the opaque wall portions in facing contact can fuse together to open an aperture therethrough.

In accordance with this invention, retention means are carried by the connector elements of the connector member for retaining the housing together. The retention means include track-defining gripper arm means positioned adjacent the first end of each housing, and flange means positioned adjacent a second end of the housing. The flange means of each housing are adapted to fit in sliding, retaining relation within the track defined by the gripper arms means of the other housing, to retain the housing together in the sealed retentive relation with the opaque wall portions in facing contact. The flange means and the tracks defined by the gripper arm means occupy a plane which is parallel to the facing opaque wall portions.

Preferably, the track-defining gripper arm means comprises an opposed pair of gripper arms positioned on one side of each connector element. Similarly, the flange means preferably comprises an opposed pair of straight flanges positioned and proportioned to be received by the gripper arms of the other connector elements.

Also, each connector element has a conduit member which communicates with the hollow interior of the housing. The conduit member in turn may be positioned in sealed relation within the bore of the flexible tubing which may communicate with a blood bag or the like so that each connector element provides a sealed end to the flexible tubing.

The outer end of the conduit member, generally positioned within the bore of the flexible tubing, preferably defines a closed end wall with a projecting member extending outwardly from the closed end wall. Accordingly, manual bending of the projecting member can cause the rupture of the end wall to permit the opening of the outer end of the conduit member.

Referring to the drawings,

FIG. 1 is an elevational view of a pair of connector elements prior to being positioned together into a sealed connector member.

FIG. 2 is a partial vertical sectional view of the connector member made from the separate connector elements of FIG. 1.

FIG. 3 is a longitudinal sectional view of a connector element of FIG. 2.

FIG. 4 is an end elevational view of a connector element of FIG. 1.

FIG. 5 is a top plan view of a connector element of FIG. 1.

FIG. 6 is an end elevational view of the connector member of FIG. 2.

FIG. 7 is a plan view of the connector element of FIG. 2.

FIG. 8 is an elevational view, taken partly in section, of a pair of connector elements of a different embodiment of this invention, prior to being joined together into a sealed connector member.

FIG. 9 is a top plan view of the connector element of FIG. 8.

FIG. 10 is a fragmentary vertical sectional view of the connector member made from the joined connector elements of FIG. 8.

FIG. 11 is a longitudinal sectional view of a single connector member of FIG. 10.

FIG. 12 is an elevational view, with parts broken away, of the joined connector elements of FIG. 10.

FIG. 13 is a plan view of the joined connector elements of FIG. 10.

Referring to FIGS. 1 through 5, a first embodiment of a connector member 10 which is made of its component connector elements 12, 14, is shown. Each of the pair of connector elements 12, 14 comprises a hollow, transparent housing 16 with the hollow interior 20 of each housing being sealable from the exterior.

A portion of the wall of each housing comprises an opaque wall portion 22 separating the hollow housing interior 20 from the exterior. Each opaque wall portion is sealed to the remainder of its transparent housing about the periphery of the wall portion 22.

Each housing 16 of the connector elements 12, 14 are adapted to be positioned together with the housing of the corresponding connector element, with the opaque wall portions 22 being positioned in facing contact with each other as shown in FIG. 2, and held in sealed, retentive relationship. Accordingly, upon exposure of the connected housing to radiant energy, in the manner described in that previously cited U.S. application Ser. No. 843,608, filed Oct. 19, 1977, the opaque wall portions in facing contact can fuse together and open an aperture therethrough.

Opaque wall portions 22 may preferably be made of an organic thermoplastic material, preferably one with a high melting or softening temperature, so that any bacteria residing upon the exterior surfaces of the opaque wall portions are killed by exposure to the melting or softening temperature of the opaque wall portion, as well as being entrapped in the melted mass. Specifically, the opaque wall portion 22 may be made of a polycarbonate material such as Lexan, sold by the General Electric Company, or various other preferably high-melting thermoplastic materials.

The thermoplastic opaque wall portion 22 generally contains a filler such as powdered charcoal, activated charcoal, or carbon black to render it opaque, although other desired fillers which are absorbant of the type of radiant energy to be used may be provided as a substitute for carbon.

Housings 16 are shown as being made of a transparent, high melting plastic material such as Lexan.

The radiant energy can be provided to the system by means of visible or incandescent, infrared, ultraviolet, or radio frequency energy as may be desired. The term "opaque" implies that the opaque wall portions are adapted to absorb a relatively high percentage of the particular radiant energy to which it is exposed. The term "transparent" implies that a lower percentage of the radiant energy applied is absorbed. Focused, infrared radiant energy is particularly desirable for use. Lasers may also be used as desired to provide the radiant energy.

Opaque wall portions 22 may be pre-stressed by uniaxial or biaxial orientation, or with radial stress patterns, to facilitate the formation of a central aperture as the opaque wall portions seal together. Also, unstressed wall portions may be used, with the central aperture formation taking place by cohesion during the heat-softening irradiation step.

Connector elements 14, 16 each carry means for retention to the other connector element. The retention means includes a pair of opposed gripper arm means 24 positioned adjacent a first end 26 of housing 16, and defining a track 28 for retaining a flange positioned within the track.

A pair of opposed flanges 30 are correspondingly positioned adjacent a second end 32 of housing 16. Each of the flanges 30 and the tracks 28 defined by the gripper arms 24 are parallel to the opaque wall portion 22. The width of the tracks 28 is proportioned to be at least as great as the width of the flanges 30, so that the flanges 30 of the opposed connector element 12, 14 can fit into the tracks of gripper arm 24, and the flanges 30 of each connector element can fit into the tracks of the gripper arms 24 of the opposed connector element. Thus, the connector elements may be held together as a connector member in sealed relationship, as shown in FIG. 2, with opaque walls 22 in facing, abutting relation.

The respective connector elements are brought together by sliding together in a relative direction which is parallel to the plane of opaque walls 22. Accordingly, accidental forces which tend to pull the connector elements apart will not cause any separation at all, since the only possibility of relative motion is in the plane of tracks 28 and flanges 30.

Appropriate detent means may be provided to cause the connector elements 12, 14 to seal together into a snapfit relationship, to prevent the separation of the connector elements into separate components after they have been assembled.

After assembly, the connector elements may be irradiated by focused infrared radiation or the like for a desired period of time. For example, when a pair of opposed 150 watt Sylvania lamps of the eliptical reflector type (Model DJL) are used, the focused infrared light may be applied for about five seconds to effectively open an aperture through the pair of opaque walls 22, at the same time causing the opaque walls to fuse together about the aperture to provide a sealed flow path between the respective hollow interiors 20 of connector elements 12, 14. If desired, the lamp may be operated at less than 150 watts by use of a lower voltage, for reduction of the irradiation intensity.

Each connector element also defines a conduit member 34 which may be integrally molded with housing 16. In this embodiment, the conduit member 34 has an axis which is in longitudinal relationship to the plane of the attached opaque wall portion 22.

Preferably, conduit member 34 is positioned in sealed relation within the bore of flexible tubing 36 which, in turn, may communicate with a sealed container 38 such as a blood bag, a parenteral solution container, or the like. Accordingly, when the connector elements 12, 14 are brought together and irradiated, a sterile connection can open between two containers 38 for communication of fluids therebetween.

Referring to FIGS. 8 through 13, another embodiment of the connector of this invention is disclosed.

FIGS. 8 through 13 show a pair of connector elements 60, 62 which comprises, as before, a hollow, transparent housing 64 and an opaque wall 66 sealed at its periphery to the transparent housing 64 in a manner which is generally similar to the previous embodiment.

Retention means are carried by each connector element for retaining the housing 64 together. The retention means include opposed gripper arms 68 adjacent first end 70 of the housing which define a track 72, for receiving a flange 74, corresponding to flanges 30 in the previous embodiment, of the connector element to which connection is to be made.

In this embodiment, opposed flange members 74 are positioned adjacent to a second end 76 of each housing 64, the flanges 74 being adapted to fit in sliding, retaining relation with a track 72 defined by the gripper arm means of another connector element, for locking of the two connector elements together, with the opaque walls 66 in facing, abutting relationship as shown in FIG. 10.

Detent means 78, 80 are provided so that the respective connector elements 60, 62, after sliding into connecting, abutting relationship, are pulled apart again only with substantial difficulty in the common mode of use where, to insure sterility, the connector elements are intended to be permanently retained together after connection during their period of use.

Each connector element 60, 62 defines an integral conduit member 84, the axis of which, in this embodiment, defines an acute angle with the plane of its associated opaque wall portion 66. As shown herein, the outer end of the conduit member 84 defines a closed end wall 86, defining a thinned, frangible area 88 which may be annular in shape. A projecting member 90 extends outwardly from the closed end wall, so that manual bending of the projecting member 90 can cause rupture of the end wall 86 to permit the opening of the outer end of conduit member 84.

As in the previous embodiment, each conduit member 84 may be positioned in sealed relation within the bore of flexible tubing 36a, which may communicate with a sealed container 38, such as a blood bag. Accordingly, manual manipulation of the flexible tubing 36a and projecting member 90 permits the rupturing of end 86 of each conduit member 84, to open the connector elements 60, 62 after they have been connected together into a connector member as shown in FIG. 10.

When both of the connector elements carry the frangibly sealed ends 86 of their conduit member, it is often desirable to open one of them prior to the irradiation step. Then, air which is in the remaining sealed chamber 94 within housing 64 and conduit member 84 will expand during the heating step, providing a pressure differential across opaque walls 66 during the irradiation step. This in turn will assist in the rupturing of the opaque walls 66 as the walls weaken and melt, to provide a preferably sterile, sealed connection between the two connector elements 60, 62.

If desired, only one of the connector elements need to carry sealed end wall 86 and elongated member 90. For example, an empty blood bag might not utilize the sealed end wall 86 and elongated member 90, while a blood bag intended for receiving blood from a donor might carry the sealed end wall, to prevent traces of blood from passing upwardly to the opaque wall 66 during storage.

Elongated member 90 may terminate in a diametric slot 92. After breaking away, the slotted end of elongated member 92 may be pressed into constricted portion 94 of tubing 36a, to hold member 92 away from broken and open end 86. This prevents occluding of the flow passage. In this instance slot 92 permits flow through constricted portion 94 while member 92 is held therein.

The above has been offered for illustrative purposes only, and is not intended to limit the invention of this application, which is as defined in the claims below.

That which is claimed is:

1. A member for sealing the end portion of a conduit, said member comprising
    transparent housing means having a hollow interior and including passage means communicating with said hollow interior and adapted for communication with the end portion of the conduit, and
    meltable opaque wall means extending across said hollow interior in a generally nonparallel direction relative to the axis of said passage means and being operative for normally sealing said hollow interior from communication with the atmosphere and for forming, in response to the subsequent application of radiant energy to melt said opaque wall means, an opening communicating with said hollow interior and the atmosphere.

2. A member for sealingly connecting the end portions of a pair of conduits, said member comprising
    housing means having transparent walls enclosing a hollow interior and including spaced first and second passage means each communicating with said hollow interior and each adapted for communication with a respective conduit end portion, and
    meltable opaque wall means extending across said hollow interior in the interval between said spaced first and second passage means and in a generally nonparallel direction relative to the axis of at least one of said first and second passage means, said opaque wall means being operative for normally blocking flow communication between said first and second passage means through said hollow interior and for forming, in response to the subsequent application of radiant energy to melt said opaque wall means, an opening establishing flow communication between said first and second passage means through said hollow interior.

3. An assembly for sealingly connecting the end portions of a pair of conduits, said assembly comprising
    first and second transparent housing means, each of said housing means having a hollow interior and including passage means communicating with said hollow interior and adapted for communication with one of the conduit end portions,
    meltable opaque wall means extending across said hollow interior of each of said first and second transparent housing means in a generally nonparallel direction relative to the axis of said associated passage means and operative for normally sealing said respective hollow interior from communication with the atmosphere and for forming, in response to the subsequent application of radiant energy to melt said opaque wall means, an opening communicating with said respective hollow interior and the atmosphere, and
    means for joining said first and second transparent housing portions together with said respective opaque wall means in abutting contact to normally block flow communication between said respective passage means through said joined hollow interiors and to form, in response to the application of radiation energy to melt each of said abutting wall means, a common opening in each of said wall means establishing flow communication between said respective passage means through said joined hollow interiors.

4. A device according to claim 1 or 2 or 3 wherein said opaque wall means forms essentially an acute angle with said passage means axis.

5. A device according to claim 4 wherein said acute angle is approximately 45°.

6. A member for sealing the end portion of a conduit, said member comprising
    transparent housing means having a hollow interior and including passage means communicating with said hollow interior and adapted for communication with the conduit end portion,
    frangible wall means in said passage means for normally preventing fluid flow therethrough,
    means operatively connected with said frangible wall means for manually fracturing said frangible wall means to permit fluid flow through said passage means, and
    meltable opaque wall means extending across said hollow interior for normally sealing said hollow interior from communication with the atmosphere and for forming, in response to the subsequent application of radiant energy to melt said opaque wall means, an opening communicating with said hollow interior and the atmosphere.

7. A member according to claim 6 wherein said opaque wall means extends in a generally nonparallel direction relative to the axis of said passage means.

8. A member for sealingly connecting the end portions of a pair of conduits, said member comprising
    housing means having transparent walls enclosing a hollow interior and including spaced first and second passage means each communicating with said hollow interior and each adapted for communication with a respective conduit end portion,
    frangible wall means in at least one of said first and second passage means for normally preventing fluid flow therethrough, means operatively connected with said frangible wall means for manually fracturing said frangible wall means to permit fluid flow through said respective passage means, and meltable opaque wall means extending across said hollow interior in the interval between said spaced first and second passage means and operative for normally blocking flow communication between said first and second passage means through said hollow interior and for forming, in response to the subsequent application of radiant energy to melt said opaque wall means, an opening establishing flow communication between said first and second passage means through said hollow interior.

9. A member according to claim 8 wherein said opaque wall means extends in a generally nonparallel direction relative to the axis of at least one of said first and second passage means.

10. An assembly for sealingly connecting the end portions of a pair of conduits, said assembly comprising
first and second transparent housing means, each of said housing means having a hollow interior and including passage means communicating with said hollow interior and adapted for communication with one of the conduit end portions,
frangible wall means in said passage means of at least one of said first and second housing means for normally preventing fluid flow therethrough,
means operatively connected with said frangible wall means for manually fracturing said frangible wall means to permit flow fluid through said respective passage means,
meltable opaque wall means extending across said hollow interior of each of said first and second transparent housing means and operative for normally sealing said respective hollow interior from communication with the atmosphere and for forming, in response to the subsequent application of radiant energy to melt said opaque wall means, an opening communicating with said respective hollow interior and the atmosphere, and
means for joining said first and second transparent housing portions together with said respective opaque wall means in abutting contact to normally block flow communication between said respective passage means through said joined hollow interiors and to form, in response to the application of radiant energy to melt each of said abutting wall means, a common opening in each of said wall means establishing flow communication between said respective passage means through said joined hollow interiors.

11. An assembly according to claim 10 wherein said opaque wall means extends in a generally nonparallel direction relative to the axis of said associated passage means.

12. A device according to claim 7 or 9 or 11 wherein said opaque wall means forms essentially an acute angle with said passage means axis.

13. A device according to claim 12 wherein said acute angle is approximately 45°.

14. A device according to claim 6 or 8 or 10 wherein said frangible wall means includes a closed end wall in said passage means, and wherein said fracturing means includes a break-away member projecting outwardly from said closed end wall and forming a part thereof.

15. An assembly adapted for connection with a container having an interior and an opening communicating with the interior and with the atmosphere, said assembly comprising
transparent conduit means adapted for communication with the container opening to establish flow communication with the container interior, said conduit means including a meltable opaque portion operative for forming, in response to the application of radiant energy to melt said opaque portion, an opening through said opaque portion and communicating with the interior of said conduit means, and
flow control means in said conduit means between said opaque portion and the container opening for normally blocking flow communication through said conduit means between the container interior and said opaque portion and selectively operative for permitting said flow communication.

16. An assembly adapted for connection with a container having an interior and an opening communicating with the interior and with the atmosphere, said assembly comprising
transparent housing means having a hollow interior,
conduit means communicating with said hollow interior and adapted for communication with the container opening to establish flow communication between the container interior and said hollow interior,
flow control means disposed in said conduit means for normally blocking said flow communication between the container interior and said hollow interior and selectively operative for permitting said flow communication, and
meltable opaque wall means extending across said hollow interior for normally sealing said hollow interior from communication with the atmosphere and for forming, in response to the subsequent application of radiant energy to melt said opaque wall means, an opening through said opaque wall means.

17. An assembly according to claim 16 wherein said opaque wall means extends in a generally nonparallel direction relative to the axis of said conduit means.

18. An assembly according to claim 17 wherein said acute angle is approximately 45°.

* * * * *